(12) United States Patent
Ouchi

(10) Patent No.: US 6,524,234 B2
(45) Date of Patent: Feb. 25, 2003

(54) TIP PORTION OF AN ENDOSCOPE

(75) Inventor: Teruo Ouchi, Saitama (JP)

(73) Assignee: Pentax Corporation, Tokyo (JP)

( * ) Notice: Subject to any disclaimer, the term of this patent is extended or adjusted under 35 U.S.C. 154(b) by 0 days.

(21) Appl. No.: 09/947,506

(22) Filed: Sep. 7, 2001

(65) Prior Publication Data

US 2002/0035311 A1 Mar. 21, 2002

(30) Foreign Application Priority Data

Sep. 18, 2000 (JP) ........................................ 2000-281156

(51) Int. Cl.⁷ ................................................ A61B 1/00
(52) U.S. Cl. ........................ 600/127; 600/129; 600/156; 606/115
(58) Field of Search ................................ 600/127, 129, 600/153, 156, 105, 175; 616/115

(56) References Cited

U.S. PATENT DOCUMENTS

| 4,436,087 A | 3/1984 | Ouchi |
| 5,976,073 A | 11/1999 | Ouchi |

FOREIGN PATENT DOCUMENTS

| JP | 58-20244 | 4/1983 | |
| JP | 11-4799 | * 1/1999 | ............ A61B/1/00 |
| JP | 11-4800 | 1/1999 | |

* cited by examiner

Primary Examiner—John Mulcahy
(74) Attorney, Agent, or Firm—Greenblum & Bernstein, P.L.C.

(57) ABSTRACT

In an endoscope, an aspirated mucosa movement regulating portion is provided in a position intermediate between the distal end and the bottom of a tip hood for ensuring that the mucous membrane aspirated from the distal end of the tip hood toward an aspiration port will not get to viewing window.

6 Claims, 3 Drawing Sheets

TIP PORTION OF AN ENDOSCOPE

BACKGROUND OF THE INVENTION

The present invention relates to the tip portion of an endoscope having a tubular tip hood provided at the distal end of an insertion portion.

In endoscopic mucosectomy, the mucosa of a diseased part in a body cavity is aspirated into the tip hood of an endscope so that it becomes like a "polyp" in shape and its base is cut off with a high frequency snare or the like.

A problem with this technique is that when the mucosa is TO aspirated into the tip hood of the endoscope, it comes so close to the viewing window of the endoscope that endoscopic examination is not possible at all. As a result, the surgeon has to perform "blind" cutting with a high frequency snare or the like and he has the risk of either excising a too narrow area of the mucosa or piercing it by removing a too wide area.

SUMMARY OF THE INVENTION

An object, therefore, of the present invention is to provide the tip portion of an endoscope by which the mucosa of a diseased part aspirated into a tip hood can be safely excised or otherwise treated under examination with the endoscope.

In the present invention, an aspirated mucosa movement regulating portion is provided in a position intermediate between the distal end and the bottom of a tip hood for ensuring that the mucous membrane aspirated from the distal end of the tip hood toward an aspiration port will not get to a viewing window. Given this design, the mucous membrane will not interfere with the visual field even if it is aspirated into the tip hood, so the mucosa of a diseased part aspirated into the tip hood can be safely excised or otherwise treated under examination with an endoscope.

The present invention provides, as a preferred embodiment, the tip portion of an endoscope having a tubular tip hood provided at the distal end of an insertion portion, with at least a viewing window and an aspiration port being provided in a position corresponding to the bottom of the tip hood, characterized in that an aspirated mucosa movement regulating portion is provided in a position intermediate between the distal end and the bottom of the tip hood for ensuring that the mucous membrane aspirated from the distal end of the tip hood toward the aspiration port will not get to the viewing window.

A treatment tool projecting port for causing treatment tools to project may be provided either to double as the aspiration port or separately therefrom and this ensures that the mucosa as aspirated into the tip hood can be excised or otherwise treated by treatment tools.

If desired, the aspirated mucosa movement regulating portion may be an annular wall formed along the inner periphery of the tip hood to project inwardly. Alternatively, the aspirated mucosa movement regulating portion may be a partition provided in the intermediate position of the tip hood to project inwardly from its inner periphery so as to provide a division at least between the space ahead of the viewing window and the space ahead of the aspiration port. In yet another embodiment, the aspirated mucosa movement regulating portion may be a wall member generally parallel to the bottom plane of the tip hood, with an opening formed in an area positioned ahead of the treatment tool projecting port.

If the tip hood is transparent, the outside of it can be examined through the viewing window.

The present disclosure relates to the subject matter contained in Japanese patent application No. 2000-281156 (filed on Sep. 18, 2000), which is expressly incorporated herein by reference in its entirety.

DESCRIPTION OF THE PREFERRED EMBODIMENT

Several embodiments of the invention are described below with reference to the accompanying drawings.

Figure 1:
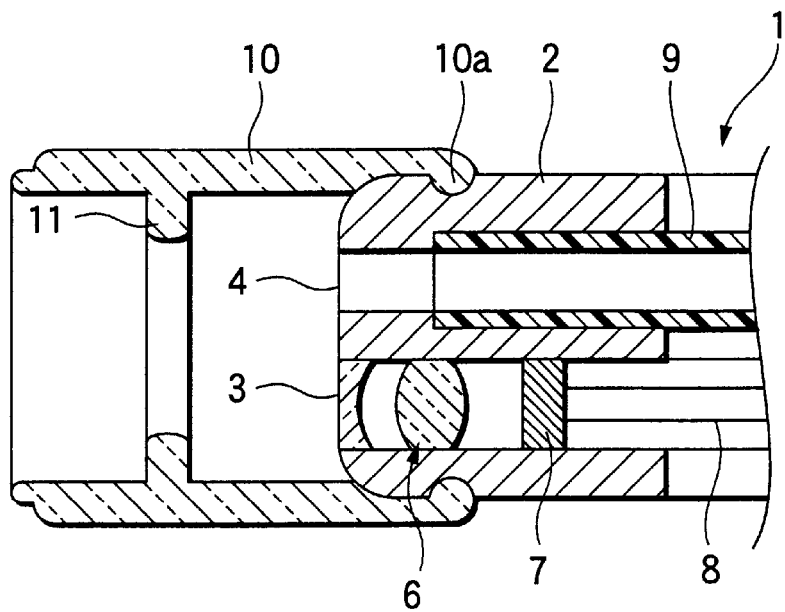
FIG. 1 is a longitudinal section of the tip portion of an endoscope according to a first embodiment of the invention.

FIG. 1 shows the tip portion of an endoscope according to a first embodiment of the invention. It comprises an insertion portion 1 in a flexible tubular form that is fitted with a cylindrical tip body 2 at the distal end, which in turn has a viewing window 3 provided in the distal end face for examining the area ahead of the tip body 2. Although not shown, illumination windows through which light for illuminating the object of interest issues are provided in the distal end face of the tip body 2 in juxtaposition with the viewing window 3.

Behind the viewing window 3 are provided objective optics 6 and the imaging plane of a solid-state imaging device 7 is provided in the position where the image of the object is formed by the objective optics 6. Indicated by 8 is a signal cable for transmitting imaging signals and the like. The solid-state imaging device 7 may be replaced by an image guide fiber bundle.

Indicated by 9 is an aspiration tube extending through the insertion channel 1 and has an aspiration port 4 open at the distal end such that it is directed forward to the distal end face of the tip body 2 in juxtaposition with the viewing window 3.

Aspiration tube 9 doubles as a treatment tool insertion channel for guiding the passage of treatment tools. Hence, the aspiration port 4 doubles as a treatment tool projecting port and the tip portion of a treatment tool inserted into the aspiration tube 9 from the side closer to the surgeon projects forward through the aspiration port 4.

The tip body 2 is fitted with a tip hood 10 at the distal end. The tip hood 10 is a cylindrical member formed typically of an elastic transparent material and it is detachably provided in such a way as to project forward from the tip body 2.

Hence, the distal end face of the tip body 2 corresponds to the base plane of the tip hood 10. Indicated by 10a is a circumferential projection that is formed on the inner periphery of the tip hood 10 at the rear end in such a way that it deforms elastically to come into or out of engagement with a groove formed in the outer periphery of the tip body 2.

In the intermediate position of the tip hood 10 which is between the distal end face of the tip body 2 corresponding to the bottom plane of the tip hood 10 and its distal end, an aspirated mucosa moving regulating portion 11 is formed in order to ensure that the mucosa aspirated from the distal end of the tip hood 10 toward the aspiration port 5 will not get to the viewing window 3.

In the first embodiment, the aspirated mucosa movement regulating portion 11 is an annular wall formed along the inner periphery of the tip hood 10 to project inwardly as a flange and it is formed as an integral part of the tip hood 10.

Figure 2:
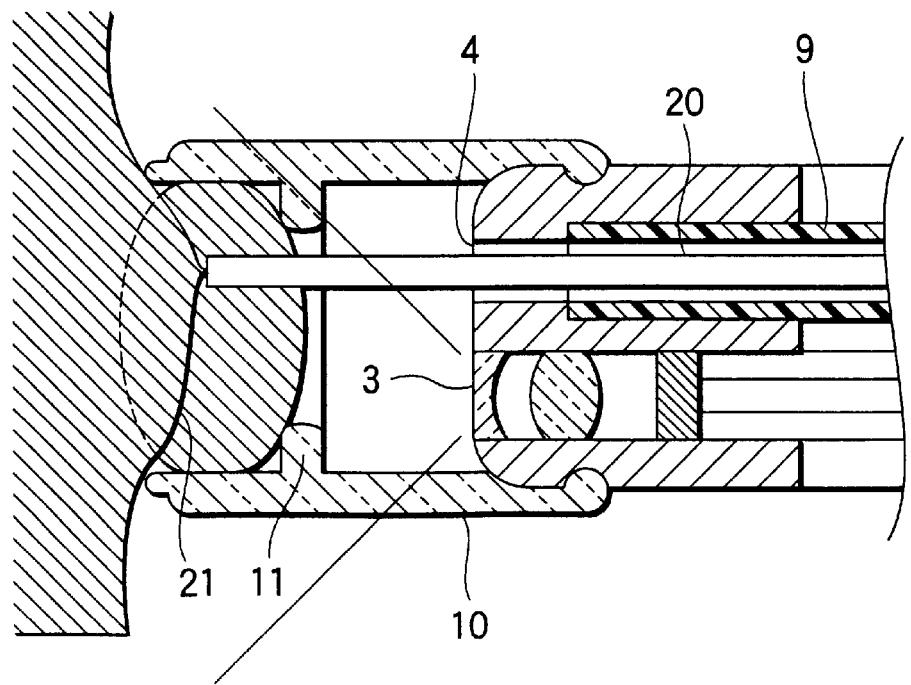
FIG. 2 is a longitudinal section showing the tip portion of an endoscope in use mode according to the first embodiment of the invention.

FIG. 2 shows the tip portion of an endoscope in use mode according to the first embodiment. As shown, the distal end of the tip hood 10 is held against the mucosa of the diseased part and vacuum is drawn into the aspiration tube 9 through the aspiration port 4, whereby the mucosa of the diseased part is sucked into the tip hood 10.

The sucked portion of the mucosa becomes like a "polyp" in shape but since its projecting end contacts the aspirated mucosa movement regulating portion 11, it will not be further aspirated into the tip hood 10 but maintains a certain distance from the viewing window 3.

As a result, the viewing window 3 provides a sufficient visual field for observing the mucosal surface of the diseased part within the tip hood 10 and, at the same time, the transparency of the tip hood 10 permits the outside of it to be examined through the viewing window 3.

A high frequency snare 20 that projects from the treatment tool projecting port (which doubles as aspiration port 4) has a loop 21 at the distal end, which is tightened to cut away the mucosa of the diseased part. The cutting operation presents no danger since it can be done under examination of the mucosa of the diseased part. Until after the environment for its use has been established, the snare loop 21 should be held in engagement with a suitable site such as the outer surface of the tip hood 10 at the distal end.

Figure 3:
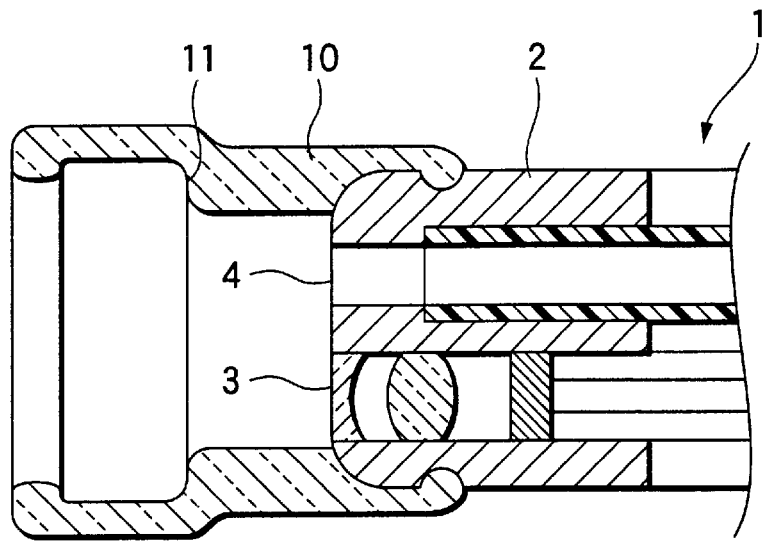
FIG. 3 is a longitudinal section of the tip portion of an endoscope according to a second embodiment of the invention.

FIG. 3 shows the tip portion of an endoscope according to a second embodiment of the invention. The tip hood 10 has a small-diameter portion formed by an aspirated mucosa movement regulating portion 11 which is an annular wall formed along the inner periphery of the tip hood 10 to project inwardly. This second embodiment brings about entirely the same advantage as the first embodiment.

Figure 4:
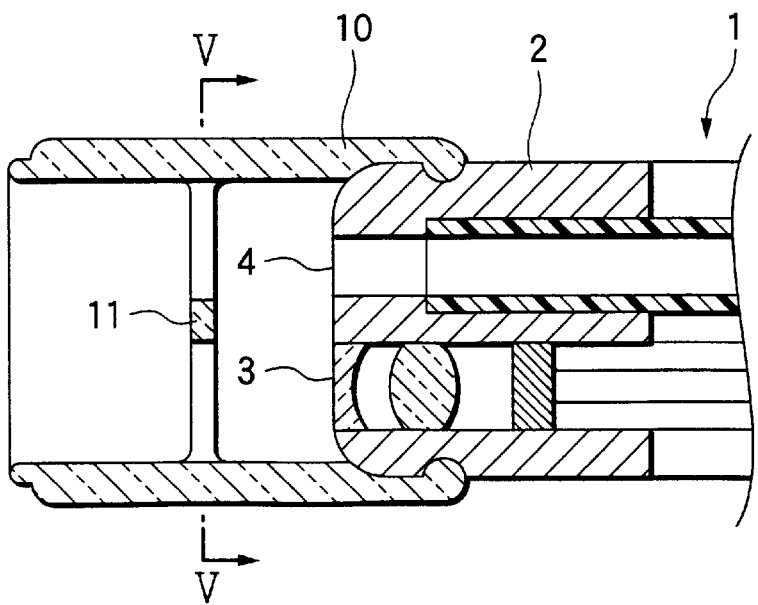
FIG. 4 is a longitudinal section of the tip portion of an endoscope according to a third embodiment of the invention.
Figure 5:
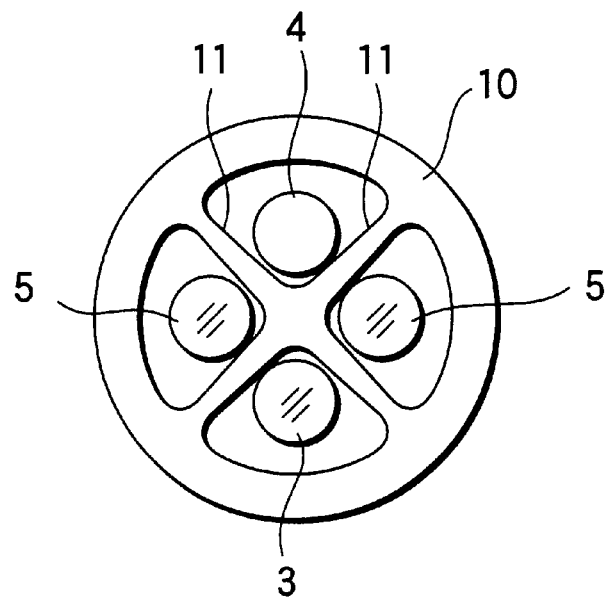
FIG. 5 is section V—V of FIG. 4.

FIG. 4 shows the tip portion of an endoscope according to a third embodiment of the invention, and FIG. 5 is section V—V of FIG. 4. In this embodiment, the aspirated mucosa movement regulating portion 11 is formed as a partition provided in the intermediate position of the tip hood 10 to project inwardly from its inner periphery so as to provide a division at least between the space ahead of the aspiration port 4 and other spaces.

As FIG. 5 shows, the aspirated mucosa movement regulating portion 11 in partition form is shaped like a cross that divides the space behind it into four sections corresponding to the aspiration port 4, two illumination windows 5 and the viewing window 3, respectively. As a result, the mucosa aspirated toward the aspiration port 4 from the distal end of the tip hood 10 is blocked by the aspirated mucosa movement regulating portion 11 to make no further movement toward the viewing window 3 and the illumination windows 5.

Figure 6:
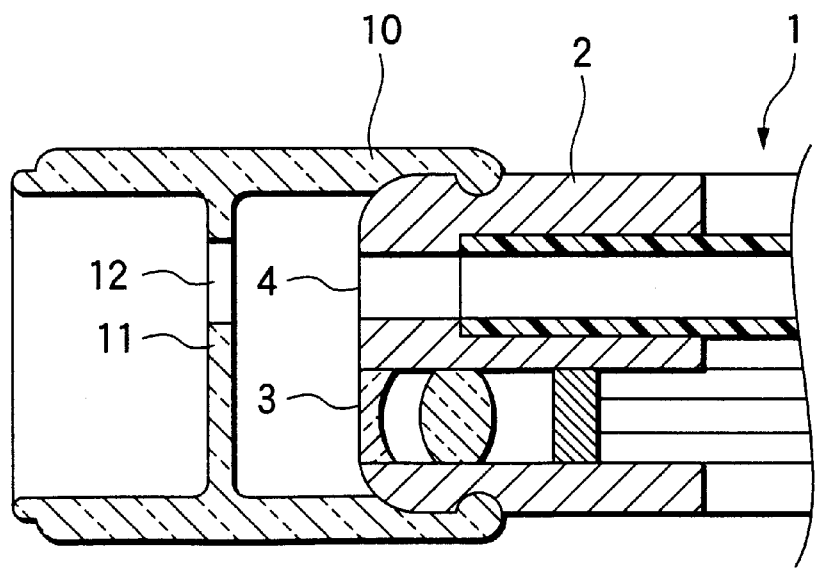
FIG. 6 is a longitudinal section of the tip portion of an endoscope according to a fourth embodiment of the invention.

FIG. 6 shows the tip portion of an endoscope according to a fourth embodiment of the invention. The aspirated mucosa movement regulating portion 11 in this embodiment is a wall member generally parallel to the distal end face of the tip body 2, with an opening formed in an area positioned ahead of the treatment tool projecting port (which doubles as the aspiration port 4). Again, the mucosa aspirated toward the aspiration port 4 from the distal end of the tip hood 10 is blocked by the aspirated mucosa movement regulating portion 11 to make no further movement toward the viewing window 3.

The present invention is by no means limited to the foregoing embodiments and various other modifications can be made by, for example, providing the treatment tool projecting port as a separate member from the aspiration port 4 or as a member external to the tip hood 10.

What is claimed is:

1. A tip portion of an endoscope having a tubular tip hood provided at the distal end of an insertion portion, with at least a viewing window and an aspiration port being provided in a position corresponding to the bottom of said tip hood, wherein an aspirated mucosa movement regulating portion is provided in a position intermediate between the distal end and the bottom of said tip hood for ensuring that the mucous membrane aspirated from the distal end of said tip hood toward said aspiration port will not get to said viewing window.

2. The tip portion of an endoscope according to claim 1, wherein a treatment tool projecting port for causing treatment tools to project is provided either to double as said aspiration port or separately therefrom.

3. The tip portion of an endoscope according to claim 2, wherein said aspirated mucosa movement regulating portion is a wall member generally parallel to the bottom plane of said tip hood, with an opening formed in an area positioned ahead of said treatment tool projecting port.

4. The tip portion of an endoscope according to claim 1, wherein said aspirated mucosa movement regulating portion is an annular wall formed along the inner periphery of said tip hood to project inwardly.

5. The tip portion of an endoscope according to claim 1, wherein said aspirated mucosa movement regulating portion is a partition provided in the intermediate position of said tip hood to project inwardly from its inner periphery so as to provide a division at least between the space ahead of said viewing window and the space ahead of said aspiration port.

6. The tip portion of an endoscope according to claim 1, wherein said tip hood is transparent.

* * * * *